United States Patent
Spicer et al.

(10) Patent No.: US 10,669,487 B2
(45) Date of Patent: Jun. 2, 2020

(54) PROCESS AND APPARATUS FOR REDUCING THERMAL SHOCK IN A HYDROCARBON STEAM CRACKING FURNACE

(71) Applicant: ExxonMobil Chemical Patents Inc., Baytown, TX (US)

(72) Inventors: David Spicer, Houston, TX (US); Philippe J. Le Roy, Houston, TX (US); George Stephens, Huffman, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 16/194,086

(22) Filed: Nov. 16, 2018

(65) Prior Publication Data

US 2019/0085249 A1 Mar. 21, 2019

Related U.S. Application Data

(62) Division of application No. 15/064,901, filed on Mar. 9, 2016, now Pat. No. 10,160,919.

(60) Provisional application No. 62/221,307, filed on Sep. 21, 2015.

(30) Foreign Application Priority Data

Oct. 30, 2015 (EP) .................................... 15192280

(51) Int. Cl.
*C10G 9/20* (2006.01)
*F27B 1/28* (2006.01)
*C07C 4/04* (2006.01)
*C10G 9/36* (2006.01)
*F23N 5/24* (2006.01)
*C10G 9/16* (2006.01)

(52) U.S. Cl.
CPC ................ *C10G 9/206* (2013.01); *C07C 4/04* (2013.01); *C10G 9/16* (2013.01); *C10G 9/36* (2013.01); *F23N 5/245* (2013.01); *F27B 1/28* (2013.01); *C10G 2300/1044* (2013.01); *C10G 2300/1081* (2013.01); *C10G 2400/20* (2013.01); *F23J 2213/70* (2013.01)

(58) Field of Classification Search
CPC . C10G 9/206; C10G 9/16; C10G 9/36; C10G 2300/1044; C10G 2300/1081; C10G 2400/20; F23N 5/245; F27B 1/28; C07C 4/04; F23J 2213/70
See application file for complete search history.

(56) References Cited

U.S. PATENT DOCUMENTS 2,635,565 A * 4/1953 Hersh ...................... F23L 17/00
110/162
4,204,833 A * 5/1980 Kmetz ..................... F23N 1/065
431/22

(Continued)

*Primary Examiner* — Ali Z Fadhel

(57) ABSTRACT

A method and apparatus of reducing thermal shock in one or more radiant tubes of a pyrolysis furnace is provided. The apparatus is a furnace comprising a blower and blower bypass conduit providing separate fluid communication paths for flue gas from the convection section to a natural draft flue gas stack. The method comprises the steps of: redirecting at least a portion of the flue gas through the blower bypass conduit when a blower shut-off event is indicated as well as reducing the firing rate of the furnace.

4 Claims, 1 Drawing Sheet

(56) References Cited

U.S. PATENT DOCUMENTS

| | | | | |
|---|---|---|---|---|
| RE30,936 E | * | 5/1982 | Kmetz | ............... F23N 5/245 |
| | | | | 431/22 |
| 2005/0261534 A1 | * | 11/2005 | Stell | ............ C10G 9/00 |
| | | | | 585/648 |
| 2006/0089519 A1 | * | 4/2006 | Stell | ............ C10G 9/00 |
| | | | | 585/648 |

* cited by examiner

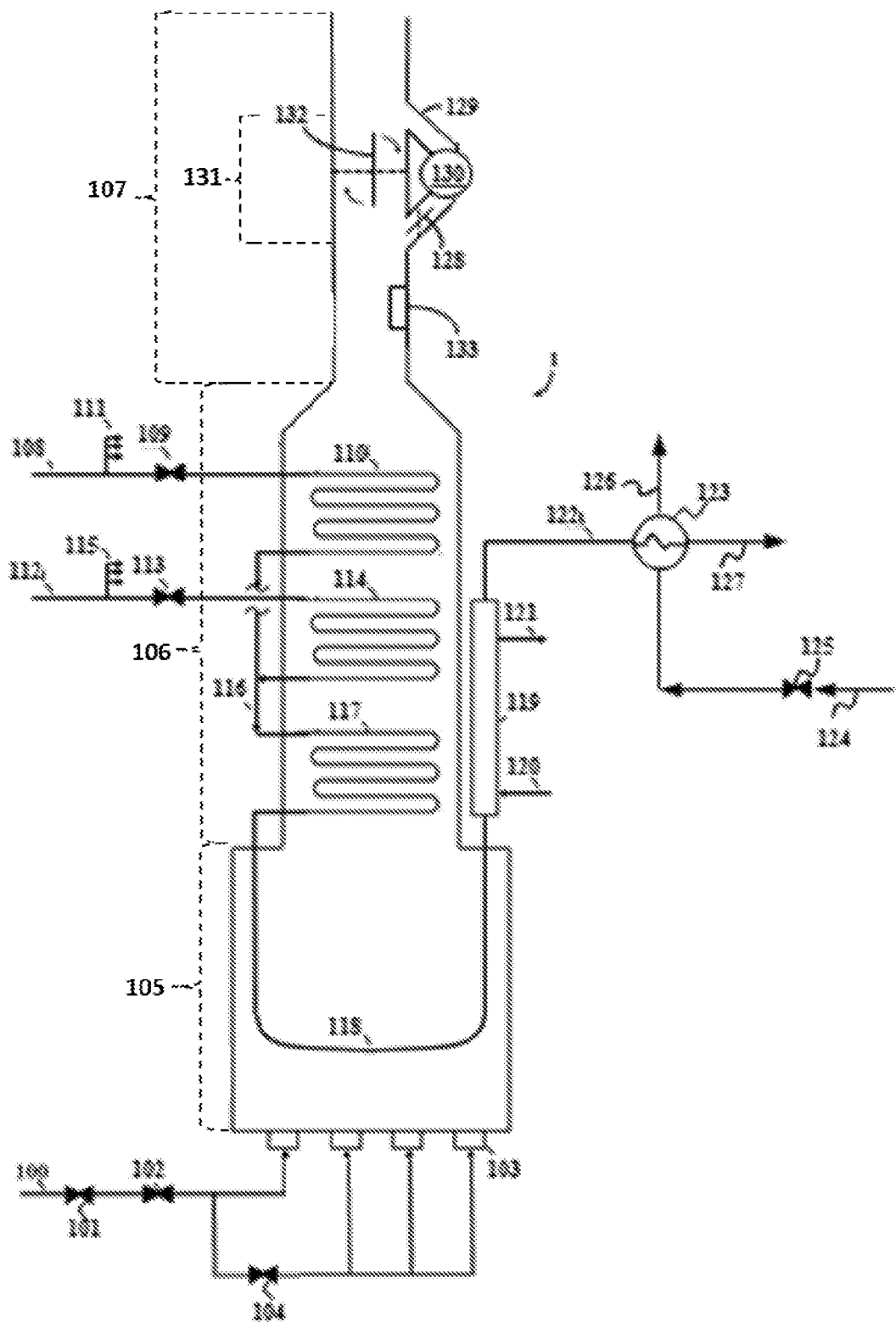

PROCESS AND APPARATUS FOR REDUCING THERMAL SHOCK IN A HYDROCARBON STEAM CRACKING FURNACE

CROSS REFERENCE TO RELATED APPLICATIONS

This application is a Divisional Application which claims the benefits of and priorities to U.S. Ser. No. 15/064,901, filed Mar. 9, 2016. This application also claims the benefits of and priorities to U.S. Ser. No. 62/221,307, filed Sep. 21, 2015, and EP European Patent Application No. 15192280.4, filed Oct. 30, 2015, the disclosures of which are incorporated by reference in their entireties.

FIELD OF THE INVENTION

The present invention relates to the field of thermal cracking hydrocarbons for the production of olefins, particularly low molecular weight olefins such as ethylene. More particularly the invention relates to methods and equipment for reducing thermal shock to steam cracking furnace tubes.

BACKGROUND OF THE INVENTION

Thermal cracking of hydrocarbon feeds in the presence of steam ("steam cracking") is a commercially important technology for producing light olefins such as ethylene, propylene, and butadiene. Hydrocarbon feeds can include one or more of ethane, propane, butane, naphtha, heavy gas oils, and crude oil. Steam cracking furnaces for carrying out steam cracking generally include a convection section, a radiant section located downstream of the convection section, and a quenching stage located downstream of the radiant section with respect to the flow of hydrocarbon feeds. At least one burner is included in the steam cracking furnace for providing heat to the convection and radiant sections. The burner(s) are located in at least one firebox, the firebox being proximate to the radiant section, with the convection section being located downstream of the radiant section with respect to the flow of heated combustion gases ("flue gas") produced by the burner. Tubular coils ("tubes") are utilized for conveying the hydrocarbon feed, steam, and mixtures thereof through the furnace's convection and radiant sections where the hydrocarbon is cracked to produce a steam cracked effluent. The steam cracked effluent is quenched and conducted away for further processing to produce the light olefins.

The hot flue gas generated by the burners is conducted away from the firebox through the convection section and discharged to atmosphere via a flue gas stack. A negative pressure (also called "draft") is generated in the flue gas stack to facilitate proper combustion and flue gas removal. Additionally, the draft is maintained for safety reasons to prevent hot flue gas from exiting through any openings in the firebox, such as, at an open visual inspection port. Maintaining draft ensures ambient air flows in through any firebox openings instead of hot flue gas exiting the firebox anywhere other than out the stack.

Some steam cracking furnaces are natural draft meaning they rely on the height of the stack and differences between hot flue gas density and density of the cooler ambient air to generate draft. Natural draft furnaces are not preferred in steam cracking because very tall stacks must be designed to provide sufficient draft to meet the desired firing rate or rate of heat generation. Many modern steam cracking furnaces are designed to use a fan or blower as the means of generating draft and have only a very short stack located at the discharge of the blower. In these cases, if the blower ceases operation, either due to mechanical issues or loss of the driving power source, the furnace will lose draft. The flue gas pressure inside the furnace will rise to above ambient pressure. It is normal practice to have pressure sensors located on the furnace which identify when the pressure rises above ambient pressure, and an automatic trip or safety-interlock system that will shut off the fuel supply to the furnace in such a situation. If the full fuel supply is shut off instantaneously, the furnace temperatures will cool down very rapidly, including the temperatures of the radiant tubes. This rapid cool down, by itself, is detrimental to service life of the tubes as contraction and expansion lead to metal fatigue. However, the metal fatigue is exacerbated by the presence of coke formed inside tube walls.

During normal cracking operation the process forms coke on the inside of the radiant tubes. Coke has a coefficient of thermal expansion that is about an order of magnitude lower than that of the radiant section tube material. During a blower shut-off event (e.g., blower failure), the radiant tubes may experience a large, sometimes rapid reduction in temperature. The differential in the coefficient of thermal expansion between the tube metal and the coke layer causes significant physical/mechanical stresses in both materials. If the coke layer is thin, the tube contracts more than the coke crushing the coke within. However, if the coke is thick and the tube metal weakened, the tubes may split and fracture around the coke. Either way, these mechanical and physical stresses lead to tube degradation known as thermal shock. Thus, thermal shock significantly reduces tube lifetime, requiring process down-time, and expenditure of significant capital costs in furnace repair. This issue is most important in ethane cracking, as the coke formed in ethane cracking is the hardest coke formed in steam cracking.

Therefore, a furnace design and process of operating a furnace that reduces or prevents thermal shock is desirable.

SUMMARY OF THE INVENTION

It has been found that thermal shock during a blower shut-off event can be reduced by providing a tall natural draft flue gas stack, conducting a portion of flue gas around the blower to the stack through a blower bypass conduit, and reducing the amount of flue gas generated. The tall stack develops draft to allow sufficient flue gas generation to maintain the radiant tubes near operating temperature and avoid thermal shock when an undesired blower shut-off event occurs. The blower bypass conduit allows the flue gas to be redirected around the blower when the blower stops operating. A set of dampers can facilitate conducting flue gas through either the blower, blower bypass conduit, or both. A control system and sensor can identify a blower shut-off event and take action.

In one aspect, embodiments of the invention provide a method of reducing thermal shock in one or more radiant tubes of a furnace. The furnace comprises a firebox with one or more burners and one or more radiant tubes, a convection section in fluid communication with the firebox, a flue gas stack, a blower, and a blower bypass conduit. The blower and blower bypass conduit provide separate fluid communication paths so flue gas may travel between the convection section and the flue gas stack through either or both paths. The method comprises several steps: First, provide fuel to the furnace. Second, combust the fuel in the firebox burners to generate flue gas. Third, use the blower to conduct the flue gas away from the firebox through the convection section, blower, and out the flue gas stack. Fourth, monitor a parameter indicative of an imminent or present blower shut-off event. Fifth, when the parameter indicates a blower shut-off event, direct at least a portion of the flue gas from the convection section through the blower bypass conduit instead of directing that portion through the blower. Finally, reduce the amount of flue gas generated in the firebox.

In another aspect, embodiments of the invention provide a furnace comprising several components. First, the furnace comprises a plurality of hydrocarbon feed conduits and a plurality of dilution steam conduits. The individual steam conduits are in fluid communication with their corresponding hydrocarbon feed conduits. Second, the furnace comprises a plurality of radiant tubes in fluid communication with the combined steam and hydrocarbon feed conduits. The furnace also comprises a firebox. The firebox comprises a plurality of burners for generating flue gas used to heat the exterior of the radiant tubes. The burners heat the radiant tubes providing a cracked hydrocarbon effluent. Third, the furnace comprises a convection section in fluid communication with the firebox for heating the hydrocarbon feed and steam conduits with flue gas generated by the burners. Fourth, the furnace comprises a flue gas stack, a blower, and a blower bypass conduit. The blower and the blower bypass conduit provide separate fluid communication paths for flue gas to flow from the convection section to the flue gas stack. Fifth, the furnace comprises a first damper adapted to control flow of flue gas through the blower and a second damper adapted to control flow of flue gas through the blower bypass conduit. Sixth, the furnace comprises a partial trip valve configured to reduce flue gas generation (by reducing fuel flow) to one or more of the plurality of burners. Seventh, the furnace comprises at least one sensor configured to detect a parameter indicative of a blower shut-off event and a controller in communication with the sensor. The controller is configured to perform the following steps when the sensor indicates a blower shut-off event: (i) close the first damper to reduce flow of flue gas through the blower, (ii) open the second damper to direct at least a portion of the flue gas through the blower bypass conduit, and (iii) close the partial trip valve to reduce flue gas generation.

BRIEF DESCRIPTION OF THE DRAWINGS

The invention is further explained in the description that follows with reference to the drawing illustrated, by way of non-limiting examples, various embodiments of the invention wherein:

FIG. 1 illustrates a schematic flow diagram in a steam cracking furnace according to an exemplary embodiment.

DETAILED DESCRIPTION

Various aspects will now be described with reference to specific embodiments selected for purposes of illustration. It will be appreciated that the spirit and scope of the process and system disclosed herein is not limited to the selected embodiments. Moreover, it is to be noted that the FIGURE provided herein are not drawn to any particular proportion or scale, and that many variations can be made to the illustrated embodiments. Reference is now made to the FIGURE, wherein like numerals are used to designate like parts throughout. When an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

Referring now to FIG. 1, a non-limiting exemplary embodiment of a steam cracking furnace 1 is illustrated. Fuel comprising gas or liquid hydrocarbon fuel is provided via conduit 100 and through shut-off valve 101 and control valve 102 At least a portion of the fuel passes through valve 102 to at least one of a plurality of burners 103 that provide radiant heat to produce the desired products by thermal cracking of hydrocarbon feed. A second portion of the fuel is directed through partial trip valve 104 to at least one of the plurality of burners 103. The burners 103 heat firebox 105 and generate hot combustion gas ("flue gas") that flows upward through the convection section 106 and then out of the furnace to atmosphere via the flue gas stack 107.

During typical pyrolysis operation, the hydrocarbon feed is conducted via conduit 108 and control valve 109 to a preheating conduit 110 in convection section 106 where the feed is preheated by indirect contact with hot flue gas generated by burners 103. The feed may be any feed suitable for steam cracking. Feedstocks that may be employed herein may be any feedstock adapted for cracking insofar as they may be cracked into various olefins, and may contain heavy fractions such as high-boiling fractions, evaporation residuum fractions, and crude oil fractions. For example, the feed may comprise $C_1$-$C_4$ hydrocarbons. The invention is particularly advantageous for feeds comprising ≥50 wt % ethane, e.g., ≥60 wt % ethane, ≥70 wt % ethane, ≥80 wt % ethane, ≥90 wt % ethane as these feeds tend to form the hardest coke during steam cracking.

A plurality of feed conduits 111 are arranged in parallel. Although not shown, each of the plurality of feed conduits 111 may be provided with a control valve 109. Each of the plurality of conduits 111 is in fluid communication with a corresponding preheating conduit (not shown) in parallel to preheating conduit 110 in convection section 106. The use of the term "plurality of conduits" is meant to refer to the fact that the convection section 106 is arranged wherein each multiple preheating conduit bank has at least two conduits in parallel. Four conduits are represented in FIG. 1, although furnaces having 3, 4, 6, 8, 10, 12, 16, 18 parallel conduits are known.

After the preheated hydrocarbon feed exits the preheating conduit 110, the preheated hydrocarbon feed is mixed with dilution steam. Dilution steam is provided via conduit 112 through control valve 113 to steam preheating conduit 114 in convection section 106 where the dilution steam is preheated by indirect contact with hot flue gas. Dilution steam is added to provide the amount of $H_2O$ required to achieve the desired hydrocarbon partial pressure during pyrolysis reaction. A plurality of steam conduits 115 may be provided corresponding to the plurality of feed conduits 111.

The mixture of dilution steam and preheated hydrocarbon feed is conducted via conduit 116 to heat exchange conduit 117 in convection section 106. Optionally for hydrocarbon feeds containing resids, the dilution steam and preheated hydrocarbon feed mixture can be conducted to a vapor liquid separator (not shown) to remove non-volatile hydrocarbon components that promote coking when cracked. A plurality of heat exchange conduits (not shown) may be provided.

Upon exiting the heat exchange conduit 117, the heated mixture is passed to radiant tube 118 in the radiant section of firebox 105 for thermal cracking of the hydrocarbon. A plurality of radiant tubes (not shown) may be provided. The temperature of the heated mixture exiting conduit 117 is generally designed to be at or near the point where significant thermal cracking commences. The temperature of the thermally cracked hydrocarbon exiting the radiant coil 118 can vary from about 788° C. (1450° F.) for some very heavy gas oil feeds to about 900° C. (1650° F.) for ethane or propane feeds. Typically, it is desirable to maintain the temperature of the radiant tubes above about 788° C. (1450° F.) to avoid thermal shocking.

After the desired degree of thermal cracking has been achieved, the furnace effluent is rapidly cooled. For this purpose, the furnace effluent is conducted to one or a series of more than one indirect transfer line heat exchanger(s) ("TLE") 119 where the heat energy from the furnace effluent is indirectly transferred to heat water provided via conduit 120 to produce high pressure steam conducted away via conduit 121. This technique is generally favored as the high pressure steam produced may be further superheated and used to power steam-turbines useful in the process to separate and recover ethylene from the furnace effluent.

However, for some heavy liquid feeds such as heavy naphthas and gas oils containing crude oil residues, the use of transfer line exchangers alone is not possible due to rapid fouling of the TLE 119. Crude oil and atmospheric residue often contain high molecular weight, non-volatile components with boiling points in excess of 595° C. (1100° F.). Pyrolysis of the non-volatile components of these feedstocks produces coke deposits on the inner surfaces of the TLE 119. As the TLE fouls, high pressure steam generation rates are reduced and the effluent temperature leaving the TLE 119 rises above the desired operating temperature for downstream equipment. For example, in some cases the temperature leaving the TLE 119 rises as high as 675° C. (1250° F.). In such cases, a direct oil quench connection is often required downstream of the TLE. The oil quench connection allows addition of quench oil into the furnace effluent stream to provide heat transfer from the furnace effluent directly to the injected quench oil. In such a quench connection, the furnace effluent is cooled primarily by the vaporization of the quench oil. Quenching techniques and quench fitting designs are described in U.S. Pat. Nos. 8,177,200; 3,593,968; 6,626,424; 3,907,661; 4,444,697; 3,959,420; 5,061,408; and 3,758,081, each of which is incorporated herein by reference in its entirety.

The partially cooled furnace effluent leaving TLE 119 is conducted via conduit 122 to quench system 123. Quench system 123 may be any suitable system for cooling the partially cooled furnace effluent. In some embodiments, the quench system 123 comprises a direct oil quench system. Preferred oil quench fluids include a liquid quench oil, such as an aromatic oil. Preferred aromatic oil may have a final boiling point of at least about 400° C. (750° F.). Other particularly useful liquid quench fluid may include an aromatic distillate. In other embodiments the partially cooled effluent is indirectly quenched with water. For example water may be provided via conduit 124 and valve 125. The heated water stream exits the quench system 123 via conduit 126. Cooled furnace effluent may be provided downstream recovery and/or purification processes (not shown) via conduit 127. The temperature of the cooled furnace effluent in conduit 127 should appropriate for feeding downstream separation equipment, for example, a primary fractionator (not shown) that receives furnace effluent at about 288° C. (550° F.) to 315° C. (600° F.).

Regardless of the hydrocarbon feedstock being cracked, over time an undesirable but largely unavoidable byproduct of the cracking process is the deposition of carbon deposits (coke) on the inner surfaces of the convection section preheating conduits, radiant section radiant tubes, TLEs, and even direct oil quench connections. Of primary concern is coke build up on the internal surfaces of the radiant tubes that reduces the effective cross-sectional area of the tube, thereby necessitating higher pressures to maintain a constant throughput. Since coke is an effective insulator, its formation on tube walls also must be accompanied by an increase in furnace tube temperature to maintain cracking efficiency.

Thus, the coke is typically removed by operating the furnace 1 in a decoking mode. Referring again to FIG. 1, during decoking, the hydrocarbon feed 108 is interrupted to the furnace and steam 112 continues passing through furnace 1. The cooled furnace effluent 127 is redirected away from the recovery and/or purification processes to atmosphere. Air is added via conduit 108 to the steam passing through the furnace to create a decoking feed air/steam mixture in conduit 116. The air/steam mixture is heated in radiant tubes 40 to remove at least a portion of the coke deposits by controlled combustion. The effluent from radiant tubes 118 is cooled in transfer line exchanger 119 and in quench system 123. Because the decoking process effluent is ultimately exhausted to atmosphere, it is conventional to use water coolant in quench system 123. The cooled effluent 127 is then exhausted to the atmosphere, either via a decoke drum, e.g., a cyclonic separator (not shown), or via the furnace firebox 105 and flue gas stack 107.

Under typical operation either in thermal cracking or decoking mode, the temperature of the radiant tubes 118 is at least about 788° C. (1450° F.). Maintaining this temperature is dependent in part on the generation and removal of hot flue gas. If insufficient draft (negative pressure) is developed, flue gas generation (or the firing rate) must be reduced or even stopped to avoid buildup of pressure inside the furnace firebox. Under conditions of reduced or terminated firing, however, the temperature of the radiant tubes 118 may decrease significantly, leading to thermal stresses in the tube material and reducing the integrity and/or lifetime of the tubes.

To mitigate the effects of thermal shock as may occur when firing is reduced in response to a blower shut-off event, flue gas stack 107 is configured to receive flue gas through one or both of a blower 130 or a blower bypass conduit 131. The flow of flue gas through blower 130 and blower conduit 129 is controlled with a first damper 128 configured and modulated to control pressure inside the furnace. The blower 130 may be of any suitable design. In some embodiments, blower 130 is a double suction, single discharge fan. The furnace 1 includes a blower bypass conduit 131 in fluid communication with flue gas stack 107. Preferably, the blower bypass conduit 131 is the same diameter as the flue gas stack 107. More preferably, the blower bypass conduit 131 is a portion of the flue gas stack 107. The blower bypass conduit 131 includes a second damper 132 configured to control the flow of flue gas there through. First and second dampers 128, 132 may independently be selected according to design requirements. Non-limiting examples of suitable dampers include butterfly or louvre type dampers. Flue gas stack 107 may be of any suitable design. Under normal operating conditions the first damper 128 is in an open position and the second damper 132 is in a closed position allowing at least a portion of the flue gas to pass through the blower 130. In response to a blower shut off event, second damper 132 may be opened allowing at least a portion of the flue gas to be directed through blower bypass conduit 131.

In order to generate sufficient natural draft to permit enough flue gas generation and maintain radiant tube temperature, the height (measured from the end of the furnace convection section to the top of the flue gas stack) of flue gas stack 107 may be determined according to design principles. Generally, a taller flue gas stack will have a more negative pressure. In particular embodiments, flue gas stack 107 may be ≥5 m, e.g., ≥20 m, ≥30 m, ≥40 m, ≥50 m, or ≥60 m. Additionally or alternatively, the height of the flue gas stack 107 may be ≤65 m, e.g., ≤55 m, ≤45 m, ≤35 m, ≤25 m. Particular ranges of the flue gas stack length include ranges formed by any pair of the above-enumerated values, e.g., 5 to 65 m, 20 to 55 m. Preferably the flue gas stack is ≥30 m tall.

Under normal operation, the first damper 128 and/or the blower 130 are configured such that the flow of flue gas through blower conduit 129 is greater than the flow of gas through the blower bypass conduit 131, e.g., the second damper 132 may be closed. The dampers 128 and 132 as well as blower 130 may be in electrical communication with one or more control systems (not shown) including at least one sensor 133 configured to sense one or more parameters characteristic of a blower shut-off event (e.g., pressure, electrical current, blower speed, etc.) Sensor 133 may be of any suitable type. When one or more of the control systems sense an imminent or present blower shut-off event, second damper 132 is moved to a more open position allowing flue gas flow through blower bypass conduit 131. Optionally, first damper 128 may be moved to a more closed position to further direct flue gas flow through blower bypass conduit. Draft pressure may be controlled using second damper 132 or another damper (not shown) in flue gas stack 107. In a particular embodiment, control system opens the second damper 132 when the detector 133 detects a blower shut-off event.

Redirecting flue gas through the natural draft blower bypass conduit 131 and flue gas stack 107 generally will not generate as much draft as when flue gas is routed via an operational blower 130. The firing rate (amount of flue gas generated) must be reduced. Advantageously, a furnace configured with a tall flue gas stack according to the invention permits sufficient flue gas generation to maintain radiant tube temperature. For example, upon sensing that the parameter predictive of a blower shut-off event has exceeded the predetermined value, the control system may close the first damper 128 and open the second damper 128. The control system also reduces the firing rate of the burners 103 to a level that maintains the radiant tubes at temperature to avoid thermal shock that would otherwise occur in a total furnace shutdown.

The control system may reduce the heat input to the furnace, by for example, automatically shutting off only a number of burners in the furnace ("a partial furnace trip"). For example, the control system may close or partially close partial trip valve 104 to reduce the amount of fuel provided through the valve 104 to one or more of the burners 103. In exemplary embodiments, the firing rate is reduced such that amount of fuel used to heat the firebox during a blower shut-off event (by reduction in the number of burners that are operated and/or in the amount of fuel provided to the burners) is ≤50 wt %, e.g., ≤30 wt %, or ≤about 15 wt %, of the fuel used to operate the burners under normal operating conditions when the blower is functioning.

Under such a reduced firing rate, sufficient heat is provided to keep the tubes above about 788° C. (1450° F.) to avoid undergoing thermal shock and the amount of flue gas is kept below ambient pressure by the natural draft of the flue gas stack through the second damper 132 and blower bypass conduit 131. Optionally, the control system may start a timer at the outset of the partial trip. If after a preset time the pressure inside the furnace is not below atmospheric pressure, the control system may stop the flow of all fuel to the furnace. For example, the control system may close shut-off valve 101 if the pressure inside the furnace is not below atmospheric pressure a preset amount of time after firing is partially reduced and flue gas is directed through blower bypass conduit 131.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including". And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:
1. A furnace, comprising:
(a) a plurality of hydrocarbon feed conduits;
(b) a plurality of dilution steam conduits in fluid communication with their corresponding hydrocarbon feed conduits;
(c) a plurality of radiant tubes in fluid communication with the corresponding combined steam and hydrocarbon feed conduits;
(d) a firebox comprising a plurality of burners generating flue gas for heating the exterior of the radiant tubes to provide a cracked hydrocarbon effluent from the radiant tubes;
(e) a convection section comprising the plurality of radiant tubes and is in fluid communication with the firebox for heating the hydrocarbon feed and steam conduits with flue gas;
(f) a flue gas stack, a blower, and a blower bypass conduit, wherein the blower and the blower bypass conduit provide separate fluid communication paths for flue gas to flow from the convection section to the flue gas stack;
(g) a first damper adapted to control flow of flue gas through the blower and a second damper adapted to control flow of flue gas through the blower bypass conduit;
(h) a partial trip valve configured to reduce flue gas generation in one or more of the plurality of burners;
(i) at least one sensor configured to detect a parameter indicative of a blower shut-off event; and
(j) a controller in communication with the sensor configured to perform the following steps when the sensor indicates a blower shut-off event,
 a. close the first damper to reduce flow of flue gas through the blower, b. open the second damper to direct at least a portion of the flue gas through the blower bypass conduit, and c. close the partial trip valve to reduce flue gas generation.

2. The furnace of claim 1, wherein the flue gas stack is from 5 to 65 m tall measured from the end of the convection section to the top of the flue gas stack.

3. The furnace of claim 1, wherein the flue gas stack ≥30 m tall measured from the end of the convection section to the top of the flue gas stack.

4. The furnace of claim 1, wherein the blower bypass conduit is a portion of the flue gas stack.

* * * * *